United States Patent
Goutsis et al.

(10) Patent No.: US 11,219,584 B2
(45) Date of Patent: *Jan. 11, 2022

(54) WATER-RESISTANT COSMETIC MEANS FOR TEMPORARILY CHANGING THE COLOR OF KERATIN-CONTAINING MATERIALS I

(71) Applicant: Henkel AG & Co. KGaA, Duesseldorf (DE)

(72) Inventors: Konstantin Goutsis, Juechen (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/629,659

(22) PCT Filed: Jul. 2, 2018

(86) PCT No.: PCT/EP2018/067817
§ 371 (c)(1),
(2) Date: Jan. 9, 2020

(87) PCT Pub. No.: WO2019/011697
PCT Pub. Date: Jan. 17, 2019

(65) Prior Publication Data
US 2020/0163848 A1 May 28, 2020

(30) Foreign Application Priority Data
Jul. 11, 2017 (DE) .................... 10 2017 211 853.9

(51) Int. Cl.
*A61Q 5/06* (2006.01)
*A61K 8/34* (2006.01)
*A61K 8/04* (2006.01)
*A61K 8/29* (2006.01)
*A61K 8/81* (2006.01)
*A61Q 1/10* (2006.01)

(52) U.S. Cl.
CPC .............. *A61K 8/34* (2013.01); *A61K 8/042* (2013.01); *A61K 8/046* (2013.01); *A61K 8/29* (2013.01); *A61K 8/817* (2013.01); *A61K 8/8147* (2013.01); *A61K 8/8152* (2013.01); *A61K 8/8158* (2013.01); *A61Q 1/10* (2013.01); *A61Q 5/06* (2013.01); *A61K 2800/43* (2013.01); *A61K 2800/5424* (2013.01); *A61K 2800/5428* (2013.01); *A61K 2800/59* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| 10,835,472 B2* | 11/2020 | Knappe ................ A61K 8/8158 |
| 10,835,473 B2* | 11/2020 | Knappe .................... A61K 8/19 |
| 2008/0112897 A1 | 5/2008 | Schiemann et al. |
| 2011/0104220 A1 | 5/2011 | Schmidt et al. |
| 2014/0150186 A1* | 6/2014 | Metten ................ A61K 8/8158 8/406 |
| 2018/0055758 A1 | 3/2018 | Lange et al. |

FOREIGN PATENT DOCUMENTS

| DE | 102005028388 A1 | 1/2007 |
| DE | 102009051171 A1 | 5/2011 |
| DE | 102015204154 A1 | 9/2016 |

OTHER PUBLICATIONS

Mintel, "Black Platinum Hair Styling Gel", Jun. 2017, XP002784118, Database accession No. 4903517.
Mintel, "Glitter Hair Make-up", Jul. 2010, XP002784119, Database accession No. 1363825.
Mintel, Fashion Hair Spray, Jun. 2017, XP002784120, Database accession No. 4874893.
Mintel, "Mascara", Nov. 2007, XP002784121, Database accession No. 814579.
Mintel, "Hot Mixing Glitter", Jun. 2008, XP002784122, Database accession No. 825975.
Mintel, "Silver Glitter Spray", Jan. 2008, XP002784123, Database accession No. 830780.
Mintel, "Fibre-Cream", Aug. 2012, XP002784124, Database accession No. 1875143.
Mintel, "Thrill Texture Fibre Gum", Jan. 2017, XP002784125, Database accession No. 4535503.
Mintel, "Wax", Jan. 2017, XP002784126, Database accession No. 4582085.
EPO, International Search Report issued in International Application No. PCT/EP2018/067817, dated Sep. 11, 2018.
EPO, International Search Report issued in International Application No. PCT/EP2018/067817, dated Aug. 28, 2018.

* cited by examiner

*Primary Examiner* — Jyothsna A Venkat
(74) *Attorney, Agent, or Firm* — Lorenz & Kopf, LLP

(57) ABSTRACT

Cosmetic agents for the temporary color change of keratinous surfaces, in particular human hair and human skin, contain an alcohol having 2 to 8 carbon atoms, a special anionic polymer, and a pigment. These cosmetic agents have an extremely good water resistance but can be removed without residue with a single application of surfactant-containing detergents. In addition, methods of temporary staining keratinous fibers and the skin using these agents are provided.

11 Claims, No Drawings

WATER-RESISTANT COSMETIC MEANS FOR TEMPORARILY CHANGING THE COLOR OF KERATIN-CONTAINING MATERIALS I

CROSS-REFERENCE TO RELATED APPLICATION

This application is a U.S. National-Stage entry under 35 U.S.C. § 371 based on International Application No. PCT/EP2018/067817, filed Jul. 2, 2018, which was published under PCT Article 21(2) and which claims priority to German Application No. 10 2017 211 853.9, filed Jul. 11, 2017, which are all hereby incorporated in their entirety by reference.

TECHNICAL FIELD

The technical field relates to water-resistant temporary color changing of keratinous materials, in particular, of human skin and/or human hair. In particular, the technical filed relates to cosmetic agents containing an aliphatic and/or aromatic alcohol, an anionic polymer based on acrylic acid and acrylates and a pigment. In addition, the technical field relates to methods and processes for the temporary coloring of keratin fibers and the skin using these cosmetic agents as well as the use of special anionic polymers in pigmented cosmetic agents to improve the water-resistance of these agents.

BACKGROUND

The change in the color of keratinous surfaces, especially of human skin and/or hair, is an important area of modern cosmetics. To change the hair color, the expert knows various dyeing systems depending on the dyeing requirements. For permanent, intensive colorations with good fastness properties and good gray coverage, oxidation colorants are used. Such colorants usually contain oxidation dye precursors, so-called developer components and coupler components, which under the influence of oxidizing agents such as hydrogen peroxide, between themselves form the actual dyes. Oxidation dyes are exemplified by very long-lasting dyeing results.

With the use of substantive dyes, ready-formed dyes diffuse from the colorant into the hair fiber. In comparison to the oxidative hair dyeing, the dyeings obtained with substantive dyes have a lower durability and faster leachability. Colorations with substantive dyes usually remain on the hair for a period of between about 5 and about 20 washes.

For changing the skin color, in particular for tanning the skin or for reducing unwanted age spots, various methods are known in the prior art. The tanning of the skin may, for example, be done using dyes that penetrate the skin layers and cause prolonged tanning. To reduce age spots, agents which penetrate the skin and decompose the age-related melanin accumulations are used. Again, a long-lasting change in skin color, which cannot or can only with difficulty be removed by cleaning the skin may be achieved.

In the context of modern fashion trends, however, there is also the need for color effects that can remain on the hair and/or skin only for a short period of time and can then be removed completely without residue from the hair and/or the skin in a single wash using surfactant-containing cleaners. Upon contact with water or sweat, however, the color effect should remain in order to prevent the color from running due to environmental influences, such as rain or sweat. Direct dyes diffuse more or less strongly into the hair fiber or the skin surface and survive several washes with surfactant-containing cleaning agents. This class of dyes is therefore not well suited for residue-free removal of the color effect after a single wash with surfactant-containing cleaning agents For short-term color changes to the hair and/or the skin, the use of color pigments is well-known. Color pigments are generally understood to be insoluble, coloring substances. These are present in the form of undissolved small particles in the coloring formulation and are deposited on the hair fibers and/or the skin surface only from the outside. Therefore, they can be removed without residue by a single wash with surfactant-containing cleaning agents. Various products of this type are available on the market under the name hair mascara.

Since the removal of hair mascara is possible by shampooing, they are usually designed as "leave-on" products. It is of advantage for the users of a "leave-on" product if they have a slight temporary change of hair style, at the same time as the temporary color change. Temporary styles could be, for example, designs such as curling, straightening, back-combing or setting. Temporary styles can be achieved, for example, by styling agents such as hair sprays, hair waxes, hair gels, hair fixatives, curly blow-dries, styling sprays, etc. The temporary shaping is also referred to as hair styling or styling and shaping agents are also referred to as styling agents.

Products which permit a temporary change in the color and/or shape of keratinous surfaces are already well-known in the prior art. Such products usually contain a mixture of film-forming polymers and pigments. However, the products do not have sufficient water-resistance.

Accordingly, it is desirable to provide a cosmetic agent for the temporary change in the color of hair and/or skin but that is highly resistant to external influences. It also is desirable to provide a method for the temporary styling and coloring of keratinous fibers using such as cosmetic agent. In addition, it is desirable to provide a process for the temporary coloring of skin using the cosmetic agent. Furthermore, other desirable features and characteristics will become apparent from the subsequent detailed description and the appended claims, taken in conjunction with the foregoing technical field and background.

BRIEF SUMMARY

Cosmetic agents, methods for the temporary styling and coloring of keratinous fibers, and processes for the temporary coloring of skin are provided. In an exemplary embodiment, a cosmetic agent comprises: an aliphatic alcohol having 2 to 8 carbon atoms, an aromatic alcohol having 2 to 8 carbon atoms, or a combination thereof; an anionic polymer comprising a structural unit of the formula (I) and a structural unit of the formula (II) and a structural unit of the formula (III)

-continued

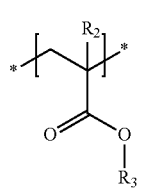

(II)

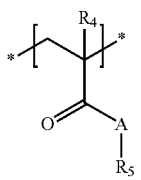

(III)

Wherein $R_1$, $R_2$ and $R_4$, independently of each other, represent a hydrogen atom or a $C_1$-$C_4$ alkyl group, $R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group, and A stands for oxygen, sulfur or an NH group; and a pigment.

In accordance with another exemplary embodiment, a method for the temporary styling and coloring of keratinous fibers comprises: providing a cosmetic agent in the form of a gel, a pump spray or an aerosol spray, the cosmetic agent comprising: an aliphatic alcohol having 2 to 8 carbon atoms, an aromatic alcohol having 2 to 8 carbon atoms, or a combination thereof, an anionic polymer comprising a structural unit of the formula (I) and a structural unit of the formula (II) and a structural unit of the formula (III)

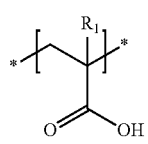

(I)

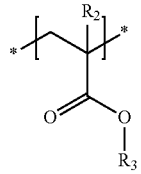

(II)

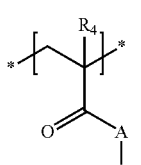

(III)

wherein $R_1$, $R_2$ and $R_4$, independently of each other, represent a hydrogen atom or a $C_1$-$C_4$ alkyl group, $R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group, and A stands for oxygen, sulfur or an NH group, and a pigment; applying the cosmetic agent to the keratinous fibers; and distributing the cosmetic agent on the keratinous fibers and styling the keratinous fibers in a desired shape.

In accordance with a further exemplary embodiment, a process for the temporary coloring of skin is provided. The process comprises: providing a cosmetic agent in the form of a gel, a pump spray or an aerosol spray, the cosmetic agent comprising: an aliphatic alcohol having 2 to 8 carbon atoms, an aromatic alcohol having 2 to 8 carbon atoms, or a combination thereof, an anionic polymer comprising a structural unit of the formula (I) and a structural unit of the formula (II) and a structural unit of the formula (III)

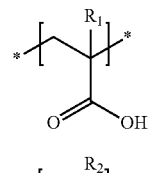

(I)

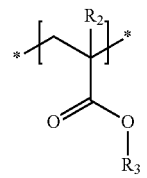

(II)

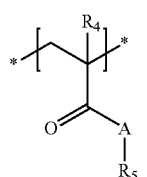

(III)

wherein $R_1$, $R_2$ and $R_4$, independently of each other, represent a hydrogen atom or a $C_1$-$C_4$ alkyl group, $R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group, and A stands for oxygen, sulfur or an NH group, and a pigment; applying the cosmetic agent to the skin, and distributing the cosmetic agent on the skin.

DETAILED DESCRIPTION

The following detailed description is merely exemplary in nature and is not intended to limit the disclosure or uses of the subject matter as described herein. Furthermore, there is no intention to be bound by any theory presented in the preceding background or the following detailed description.

The goal of the present disclosure is to provide a versatile usable mascara product, which allows temporary color change of hair and/or the skin. The product can be applied by employing a sponge, a brush or a spray application. The color change should in this way be easy and low-damage and able to be removed by a single wash with surfactant-containing cleaners from the hair and/or skin without leaving a residue. However, until the next wash, the product on the keratinous surface should be highly resistant to external influences, i.e. exposure to water or sweat, abrasion on textiles or combs should not result in color loss or other removal of the product. At the same time, the keratinous surface colored in this way should have good cosmetic properties.

Surprisingly, it has been found that this goal can be achieved by the use of color pigments and certain anionic polymers when used in a specific alcoholic carrier. The use of such polymers leads to a high water-resistance of the cosmetic agents, but without adversely affecting the cosmetic properties of these agents. In addition, the dyeing can be removed without residue by a single wash with surfactant-containing cleaning agents and therefore leads, in contrast to a dyeing with oxidation dyes and direct dyes or bleaching with oxidizing agents, only to a temporary coloration of the keratinous surfaces, especially of the skin and/or hair.

The first exemplary embodiment of the present disclosure is thus a cosmetic agent containing a) an aliphatic and/or aromatic alcohol having 2 to 8 carbon atoms,
b) an anionic polymer comprising a structural unit of the formula (I) and a structural unit of the formula (II) and a structural unit of the formula (III)

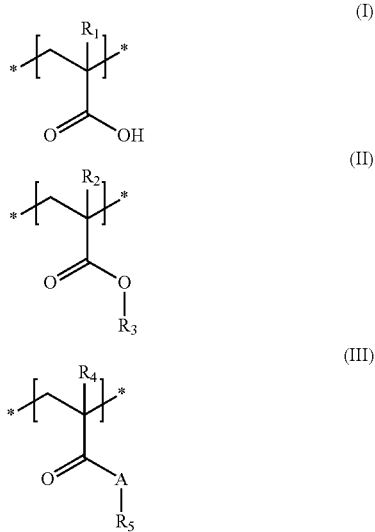

where
$R_1$, $R_2$ and $R_4$, independently of each other, represent a hydrogen atom or a $C_1$-$C_4$ alkyl group,
$R_3$ stands for a branched or unbranched, saturated or unsaturated $C_1$-$C_{12}$ alkyl group,
$R_5$ stands for a branched or unbranched, saturated or unsaturated $C_6$-$C_{14}$ alkyl group and
A is oxygen, sulfur or an NH group, and
c) a pigment.

According to the above formulas and all the following formulas, a chemical bond marked with the symbol "*" stands for a free valence of the corresponding structural fragment. Here, free valence is to be understood as meaning the number of atomic bonds which originate from the corresponding structural fragment at the position indicated by the symbol "*". In the context of the present disclosure, in each case an atomic bond primarily proceeds from the positions of the structural fragments marked with the symbol "*" to form further structural fragments.

In the context of the present disclosure, the term "anionic polymers" is understood as meaning those polymers which carry in a protic solvent under standard conditions at least one structural unit having permanently anionic groups, the anionic groups having to be compensated by counterions while maintaining electroneutrality. As contemplated herein, anionic groups are in particular carboxyl groups.

The indication "wt.-%" refers in the present case, unless stated otherwise, to the total weight of the cosmetic agents of the present disclosure, where the sum of all ingredients of the agents of the present disclosure results in about 100 wt.-%.

If the cosmetic agents of the present disclosure contain a propellant, the indication wt.-% refers to the total weight of the cosmetic agent including the propellant present.

As the first component a), the cosmetic agent of the present disclosure contains an aliphatic and/or aromatic alcohol having 2 to 8 carbon atoms. Aliphatic and/or aromatic alcohols having 2 to 8 C atoms are compounds which have 2 to 8 C atoms, are aliphatic and/or aromatic in nature and carry one or more hydroxyl groups.

The alcohols a) in the terms of the present disclosure do not carry any heteroatoms other than oxygen. They may include an ether aggregation but have, however, no functional groups other than the hydroxy group (i.e. monoethanolamide, alpha-hydroxycarboxylic acids, dihydroxyacetone, etc. are not alcohols in the sense of the present disclosure).

Suitable aliphatic alcohols are, for example, ethanol, isopropanol, n-propanol, butanol, n-pentanol, 1,2-propanediol, 1,3-propanediol, 1,3-butanediol, 1,4-butanediol, 1,2-hexanediol, 1,6-hexanediol and glycerin. Suitable aromatic alcohols are, for example, benzyl alcohol, phenoxyethanol and phenylethyl alcohol.

In an exemplary embodiment, the aliphatic and/or aromatic alcohol having 2 to 8 carbon atoms is selected from the group of ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, glycerol, benzyl alcohol, phenoxyethanol, phenylethyl alcohol and mixtures thereof.

Alcohol a) is an organic solvent which contributes to the dissolution of the anionic polymer b) and, after application of the agent to the keratinous surface, influences the rate of film formation of the polymer b). It has been found that a particularly good and uniform film formation is achieved if the alcohol in a total amount of at least about 10% wt. is included in the agent. The best results were observed with an alcohol amount of at least about 40 wt.-%. All of the quantitative data in % by weight is based on the total amount of all alcohols a) as contemplated herein, which is related to the total weight of the agent.

In an exemplary embodiment, the aliphatic and/or aromatic alcohol having 2 to 8 carbon atoms is contained in a total amount of from about 40 to about 98 wt.-%, for example, from about 50 to about 95 wt.-%, such as from about 60 to about 90 wt.-%, in particular from about 70 to about 90 wt.-%, in each case based on the total weight of the cosmetic agent.

The minimum one alcohol a) is a compound which has different boiling points and is highly volatile. It has been found that the use of ethanol leads to a particularly good film formation and thus to a particularly high adhesion of the pigments on the keratinous surface. In this case, the color result is particularly uniform and high resistance to external environmental influences such as rain, sweat and abrasion is achieved. Accordingly, in an exemplary embodiment, the cosmetic agent—based on its total weight—contains ethanol in a total amount of from about 40 to about 98 wt.-%, for example from about 50 to about 95 wt.-%, such as from about 60 to about 90 wt.-%, in particular from about 70 to about 90 wt.-%.

The properties described above can be improved even further by adding to the ethanol another polyhydric alcohol of lower volatility, for example 1,2-propanediol or glycerol. In a further embodiment, an agent as contemplated herein, based on its total weight, additionally contains 1,2-propanediol and/or glycerol in a total amount of from about 0.1 to about 7.0% by weight.-%, for example from about 0.5 to about 5.5 wt.-%, such as from about 1.0 to about 3.5 wt.-%, in particular of from about 1.5 wt.-% to about 2.5 wt.-%.

As second constituent b), as an anionic polymer which contains at least one structural unit of the formulas (I) to (III) is present in the cosmetic agent contemplated herein, in accordance with an exemplary embodiment. In the structural units of formulas (I) to (III), the radicals $R_1$, $R_2$ and $R_4$ can stand for $C_1$-$C_4$ alkyl groups. Examples of such groups are methyl, ethyl, propyl, isopropyl, hydroxypropyl, butyl, sec-butyl, isobutyl, tert-butyl and hydroxy butyl. Furthermore, the radicals $R_3$ and $R_5$ in the structural units of formulas (II) and (III) can stand for $C_1$-$C_{12}$- or $C_6$-$C_{14}$ alkyl groups. Such groups include, for example, pentyl, hexyl, heptyl, capryl, caprine, lauryl and myristyl groups.

In an exemplary embodiment, in the structural units of the formulas (I) and (III) the radicals $R_1$ and $R_4$ in each case, independently of one another, represent a hydrogen atom and in the structural unit of the formula (II) the radical $R_2$ represents a methyl group. Therefore, the use of anionic polymers based on acrylic acid, methacrylates and acrylamides or acrylates is suitable. The use of such anionic polymers leads to a particularly high water resistance of the cosmetic agents as contemplated herein.

In another exemplary embodiment, in the structural unit of the formula (II) the radical $R_3$ stands for a branched $C_3$-$C_6$ alkyl group, especially for a *—$CH_2$—$CH(CH_3)_2$-group. In this respect the * symbol indicates the connection of the radical $R_3$ with the hydrogen atom of the structural unit of formula (II). The radical $R_3$ is thus bonded via the $CH_2$ group to the carbonyl group of the structural unit of the formula (II). The use of anionic polymers, which in particular contain branched methacrylates, has proved to be particularly advantageous with regard to water resistance on the one hand and the leachability of the pigments by employing surfactant-containing cleaning agents on the other hand.

Furthermore, in another exemplary embodiment, A stands for an NH group in the structural unit of the formula (III). Suitable anionic polymers therefore contain at least one structural unit based on acrylamides. The use of anionic polymers based on acrylamides leads to an improved resistance to external environmental influences without, however, negatively influencing the leachability with surfactant-containing cleaning agents.

In an exemplary embodiment, in the structural unit of formula (III), the radical $R_5$ stands for a branched $C_6$-$C_{10}$ alkyl group, in particular for a *—$C(CH_3)_2$—$CH_2$—$C(CH_3)_3$ group. Here, the * symbol indicates the linkage of the radical $R_5$ with unit A of the structural unit of the formula (III). The use of anionic polymers, which in particular contain branched acrylamides and acrylates, has proved to be particularly advantageous with regard to water resistance on the one hand and the leachability of the pigments by surfactant-containing cleaning agents on the other hand.

As contemplated herein, anionic polymers which contain a structural unit of the formula (I), a structural unit of the formula (II) and a structural unit of the formula (III) are therefore used to particular advantage

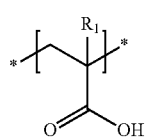

(I)

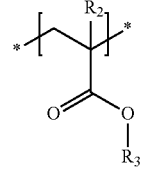

(II)

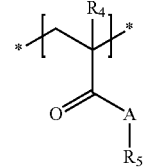

(III)

where
$R_1$ and $R_4$ each represents a hydrogen atom,
$R_2$ represents a methyl group,
$R_3$ stands for a *—$CH_2$—$CH(CH_3)_2$-group,
$R_5$ stands for a *—$C(CH_3)_2$—$CH_2$—$C(CH_3)_3$-group and
A stands for an NH group.

The use of such anionic polymers based on acrylic acid, 2-methylpropyl methacrylate and octyl acrylamide has proved to be particularly advantageous in terms of resistance to external environmental influences on the one hand and the leachability of the cosmetic agents of the present disclosure by surfactant-containing cleaning agents on the other hand. Therefore, the use of such polymers in pigment-containing cosmetics results in a water-resistant temporary color, which can be removed by a single use of surfactant-containing cleaning agents. In addition, a high and flexible hairstyle, which does not stick together when exposed to moisture thereby making an unnatural impression, can be achieved with these polymers.

Suitably used anionic polymers have certain average molecular weights $M_w$. The determination of these molecular weights can be carried out for example by coupling a gel permeation chromatography (GPC) to a Fourier transform mass spectrometer (FTMS) as in Aaserud D. J et. al; "Gel Permeation Chromatography Coupled to Fourier Transform Mass Spectrometry for Polymer Characterization"; anal. Chem. 1999, 71, 4793-4799. In an exemplary embodiment, the anionic polymer has an average molecular weight $M_w$ from about 50,000 to about 250,000 g/mol, for example from about 80,000 to about 220,000 g/mol, such as from about 100,000 to about 200,000 g/mol, in particular from about 110,000 to about 180,000 g/mol.

In other exemplary embodiments, cosmetic agents of the present disclosure comprise an anionic polymer b) in a total amount of from about 0.1 to about 10% by weight.-%, for example from about 0.5 to about 8.0 wt.-%, such as from about 1.0 to about 5.5 wt.-%, in particular from about 1.0 to about 2.5 wt.-%, based on the total weight of the cosmetic agent. The use of these amounts of the anionic polymer results in a high resistance to external environmental influences, without negatively influencing the applicability of these agents and the storage stability. When using these amounts of polymer in agents for the simultaneous temporary color and style change of the hair, a high and flexible hairstyle is made possible in addition to a water-resistant dyeing.

As a third component c), a pigment is present in an exemplary embodiment of the cosmetic agent as contemplated herein. For the purposes of the present disclosure, pigments are understood as meaning coloring compounds which have a solubility of less than about 0.1 g/l at about 20° C. in water. Water solubility can be carried out, for example, by the method described below: about 0.1 g of the pigment is weighed in a beaker. A stir bar is added. It is then made up to about 1 liter with distilled water (about 20° C.). It is stirred for an hour. If undissolved components of the pigment are still visible in the mixture after this period, the solubility of the pigment is below about 0.1 g/l.

In an exemplary embodiment, the cosmetic agents of the present disclosure provide a temporary color in the form of "metallic" effects. The white pigments do not fall under the definition of the color pigment. White pigments are achromatic inorganic pigments with a high refractive index (usually greater than about 1.8), which are usually synthesized and especially for producing optical whiteness in paints or as a filler, e.g. in plastics. White pigments such as titanium dioxide or zinc dioxide are therefore explicitly excluded from the definition of the color pigment as used herein.

In the cosmetic agents contemplated herein, the color pigments are present in the form of small undissolved particles which do not diffuse into the keratinous surface, but which accumulate in the polymer film formed by component b) on the outside of the keratinous surface.

Suitable color pigments may be organic and/or inorganic in origin. Suitable color pigments are selected from synthetic or natural inorganic pigments. Inorganic color pigments of natural origin can be prepared, for example, from chalk, ocher, umber, green earth, baked Terra di Siena or graphite. Furthermore, inorganic color pigments, black pigments such as iron oxide black, colored pigments such as ultramarine or iron oxide red and fluorescent or phosphorescent pigments can be used.

In an exemplary embodiment, the cosmetic agent contains as color pigment (c) an inorganic color pigment which is selected from (i) colored metal oxides, (ii) metal hydroxides, (iii) metal oxide hydrates, (iv) silicates, (v) metal sulfides, (vi) complex metal cyanides, (vii) metal sulfates, (viii) bronze pigments, and/or (ix) mica or mica-based colored pigments coated with at least one metal oxide and/or metal oxychloride, and x) their mixtures.

Particularly suitable are colored metal oxides, hydroxides and oxide hydrates, mixed phase pigments, sulfur-containing silicates, silicates, metal sulfides, complex metal cyanides, metal sulfates, chromates and/or molybdate. In particular, black iron oxide (C.I. 77499), yellow iron oxide (C.I. 77492), red and brown iron oxide (C.I. 77491), manganese violet (C.I. 77742), ultramarine (sodium aluminum sulfasilicate, C.I. 77007, Pigment Blue 29), chromium oxide hydrate (C.I. 77289), iron blue (Ferric Ferrocyanide, C.I. 77510) and carmine (cochineal), are all suitable pigments.

Color pigments which are also suitable as contemplated herein are colored pearlescent pigments. These are usually based on mica and/or mica-based colored pigments and may be coated with one or more metal oxides. Mica belongs to the layer silicates. Representatives of these silicates are muscovite, phlogopite, paragonite, biotite, lepidolite and margarite. To produce the pearlescent pigments in conjunction with metal oxides, the mica, predominantly muscovite or phlogopite, is coated with a metal oxide.

As an alternative to natural mica, synthetic mica coated with one or more metal oxides may also be used as pearlescent pigment. Suitable pearlescent pigments are based on natural or synthetic mica (mica) and are coated with one or more of the abovementioned metal oxides. The color of the respective pigments can be varied by varying the layer thickness of the metal oxide(s).

Accordingly, in an exemplary embodiment, the pigment is a mica-based or mica-based colored pigment which is coated with one or more metal oxides selected from the group including titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfasilicates, CI 77007, Pigment Blue 29), chromium oxide hydrate (CI 77289), chromium oxide (CI 77288) and/or iron blue (ferric Ferrocyanide, CI 77510).

Examples of particularly suitable color pigments are commercially available, for example, under the trade names Rona®, Colorona®, Xirona®, Dichrona® and Timiron® from Merck, Ariabel® and Unipure® from Sensient, Prestige® from Eckart Cosmetic Colors and Sunshine® available from Sunstar.

Suitable color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, Mica, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, Mica, TITANIUM DIOXIDE (CI 77891), D & C Red NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, Mica, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Suitable color pigments with the trade name Xirona® are, for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

Suitable color pigments with the trade name Unipure® are, for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica For some applications, the above-mentioned color pigments whose surface has been rendered hydrophobic are particularly suitable. It has been found that these pigments can sometimes be advantageous, in particular, for storage in extreme conditions.
Suitable hydrophobizing agents are, for example, silicones. Hydrophobic surface-treated color pigments are described, for example, in DE 102009051171, the contents of which are expressly incorporated herein by reference.

Because of their excellent light, weather and/or temperature resistance, the use of the abovementioned inorganic color pigments in the cosmetic agents of the present disclosure is particularly suitable.

In an exemplary embodiment, the pigments used have a particle size that, on the one hand, leads to a uniform distribution of the pigments in the polymer film formed and, on the other hand, avoids a rough hair or skin feeling after the application of the cosmetic agent. Accordingly, in a further embodiment, the pigment has an average particle size D50 from about 1.0 to about 50 μm, for example from about 5.0 to about 45 μm, such as from about 10 to about 40 μm, in particular from about 14 to about 30 μm. The mean particle size D 50 can be determined, for example, using dynamic light scattering (DLS).

Depending on which color change on the keratinous surface is desired, the color pigment c) can be used in different amounts. The more color pigment used, the higher the amount of color change in general. Above a certain amount of use, however, the adhesion of the pigment to the keratin fiber encounters a limit beyond which it is no longer possible to increase the extent of the color change by further increasing the amount of pigment used.

In this context, it has been found that when using the polymer b) as contemplated herein—in particular the suitable representatives described herein—on the keratinous surface, a film can be formed, which allows the pigments to adhere in particularly large amounts on the surface. In an exemplary embodiment, the pigment is contained in a total amount of from about 1.0 to about 25.0 wt %, for example from about 5.0 to about 20.0 wt.-%, such as from about 7.0 to about 18.0 wt.-%, in particular from about 8.5 to about 15.5 wt.-%, in each case based on the total weight of the cosmetic product.

With regard to the water resistance of the pigment-containing polymer film, it has proved to be advantageous if a specific weight ratio of polymer b) to pigment c) is contained in the cosmetic agent. In an exemplary embodiment, the cosmetic agent has a weight ratio of the anionic polymer b) to the pigment c) of from about 1.0 to about 6.0, for example from about 2.0 to about 5.5, such as from about 2.5 to about 5.0, in particular from about 3.0 to about 4.5. The weight ratio given above refers here to the total amounts of polymer b) and pigment c). If, therefore, a mixture of different polymers b) and/or pigments c) is used, then the total amount of the mixture of polymer b) and/or pigment c) is used for the calculation of the weight ratio.

In an exemplary embodiment, a cosmetic composition for the temporary reshaping of keratinous fibers contains
  a) an aliphatic alcohol having 2 to 8 carbon atoms selected from ethanol,
  b) an anionic polymer comprising a structural unit of the formula (I) and a structural unit of the formula (II) and a structural unit of the formula (III)

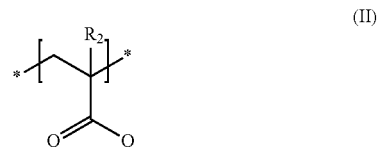

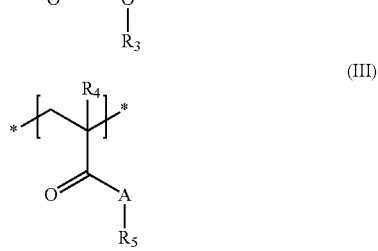

where
  $R_1$ and $R_4$ each represents a hydrogen atom,
  $R_2$ represents a methyl group,
  $R_3$ stands for a *—$CH_2$—$CH(CH_3)_2$ group,
  $R_5$ stands for a *—$C(CH_3)_2$—$CH_2$—$C(CH_3)_3$ group and
  A is an NH group.
  c) a pigment selected from mica or micabased colored pigments containing one or more metal oxides selected from the group including titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfasilicates, CI 77007, Pigment Blue 29), chromium oxide hydrate (CI 77289), chromium oxide (CI 77288) and/or iron blue (Ferric Ferrocyanide, CI 77510).

Such cosmetic agents have a high resistance to external environmental influences, such as rain, sweat, abrasion through textiles and combs, and can still be removed without residue by a single application of surfactant-containing cleaning agents. When applied to keratinous fibers, especially hair, an excellent degree of hold and high moisture resistance is also achieved. The high moisture resistance avoids sticking of the hair when exposed to moisture. When applied to the skin, these agents have good cosmetic properties and do not result in dry or oily skin.

The agents of the present disclosure contain all the essential constituents in a carrier. In particular aqueous, aqueous-alcoholic and alcoholic carriers can be used as carriers. When alcoholic carriers are used, the ingredient mentioned above forms a) the cosmetic carrier. Due to the water content of the carrier, the deposition of the pigments on the keratinous surfaces and the film formation of the polymer b) can also be influenced. If the water content is too high, there is a risk that the product will not dry sufficiently quickly. In particular, when the agents are adjusted to a lower viscosity (for example, because they are to be sprayed), the color result may be uneven. Accordingly, in an exemplary embodiment, the cosmetic agent contains water in a total amount of from 0 to about 30 wt.-%, for example from 0 to about 20 wt.-%, such as from 0 to about 10 wt.-%, in particular from 0 to about 2.0 wt. %, based on the total weight of the cosmetic agent.

The cosmetic agents of the present disclosure can be used for the simultaneous temporary color and shape change of keratinous fibers, especially hair. In addition, these agents can be used for temporary color change of the skin. For this purpose, they can be made up in the usual forms, for example as gel, spray, foam or wax. Preparation as a spray is preferred. Such sprays may be in the form of aerosols and non-aerosols and sprayed from containers known to experts. If the agents are formulated as aerosols, there is at least one additional propellant. Propellants suitable as contemplated herein are for example selected from $N_2O$, dimethyl ether, $CO_2$, air, alkanes with 3 to 5 carbon atoms, such as propane, n-butane, iso-butane, n-pentane and iso-pentane, as well as mixtures thereof. Dimethyl ether is particularly suitable as a propellant agent. This present disclosure also expressly includes the co-use of blowing agents of the fluorochlorohydrocarbon type, in particular fluorocarbons. In an embodiment, these blowing agents are present in a total quantity of from about 30 to about 70 wt. %, for example of from about 35 to about 75 wt. %, such as of from about 40 to about 60 wt. %, based on the total weight of the cosmetic agent.

The well-known, as technology stands, mascara products usually contain fatty substances. These fatty substances may also form a film on the keratinous surfaces which will protect the pigments from abrasion or washing off with water after use. The main disadvantage of the fatty substances, however, is that they produce a less favorable feel on the keratinous surface, which manifests itself in particular in a feeling of hardness and a greasy feeling. The keratinous surface seems heavy and visually gives a greasy impression.

As contemplated herein the cosmetic products contain only a small proportion of fatty substances. Accordingly, in an exemplary embodiment, the cosmetic agent contains fatty substances in a total amount of from 0 to about 2.5 wt.-%, for example from 0 to about 1.5 wt.-%, such as from 0 to about 0.5 wt.-%, for example, from 0 to about 0.1 wt.-%, in particular of 0 wt. %, based on the total weight of the cosmetic agent. For the purposes of the present disclosure, "fatty substances" are organic compounds having a solubility in water at room temperature (about 22° C.) and atmospheric pressure (about 760 mm Hg) of less than about 1% by weight, preferably less than about 0.1 wt-%. The definition of fat constituents explicitly includes only uncharged (i.e. nonionic) compounds. Charged compounds such as fatty acids and their salts are not understood as a fatty ingredient for the purposes of the present disclosure. Fatty substances have at least one saturated or unsaturated alkyl group having at least 12 carbon atoms. If the fatty substances contain an unsaturated alkyl group, this may have one or more double bonds. The molecular weight of the fat constituents is at most 5000 g/mol, for example at most 2500 g/mol, such as a maximum of 1000 g/mol. The fat components are neither polyoxyalkylated nor polyglycerylated compounds. Therefore, fatty alcohols or fatty acids which are esterified or etherified with at least two oxyalkyl groups or with at least two glycerol units, do not fall under the definition of fatty substances.

In an embodiment, fatty substances present in a total amount of at most about 2.5% by weight are selected from the group including (i) $C_{12}$-$C_{30}$ fatty alcohols; (ii) $C_{12}$-$C_{30}$ fatty acid triglycerides; (iii) diesters of one equivalent of ethylene glycol (1,2-ethanediol) with two equivalents of fatty acid (ethylene glycol difatty acid ester); (iv) waxes; (v) hydrocarbons having at least 12 carbon atoms; and (vi) mixtures thereof. $C_{12}$-$C_{30}$ fatty alcohols are saturated, mono- or polyunsaturated, linear or branched fatty alcohols containing 12 to 30 carbon atoms. Examples of such $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol). Examples of branched fatty alcohols are 2-octyl dodecanol, 2-hexyl dodecanol and/or 2-butyl dodecanol. $C_{12}$-$C_{30}$ fatty acid triglycerides are mono-, di- and triesters of the trihydric alcohol glycerol with three equivalents of fatty acid. Both structurally identical and different fatty acids within a triglyceride molecule can be involved in ester formation. Waxes are esters of $C_{12}$-$C_{30}$ fatty acids with $C_{12}$-$C_{30}$ fatty alcohols. As contemplated herein, hydrocarbons are compounds consisting exclusively of the atoms carbon and hydrogen. Examples of hydrocarbons are mineral oils, liquid paraffin oils (e.g. Paraffinium Liquidum or Paraffinum Perliquidum), isoparaffin oils, semi-solid paraffin oils, paraffin waxes, hard paraffin (Paraffinum Solidum), vaseline and polydecenes. Silicones, on the other hand, are not included in the definition of fatty substances.

As contemplated herein, the fatty substances which are not included or in the previously mentioned quantitative ranges are therefore preferably from the group of $C_{12}$-$C_{30}$ fatty alcohols, the $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, hydrocarbons and mixtures thereof.

In the following tables, exemplary embodiments AF 1 to AF 48 of the cosmetic agents as contemplated herein are listed (all data in wt.-%).

|  | AF 1 | AF 2 | AF 3 | AF 4 |
|---|---|---|---|---|
| Alcohol a) [1] | 40 to 98 | 50 to 95 | 60 to 90 | 70 to 90 |
| Anionic polymer b) [2] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Water | 0 to 30 | 0 to 20 | 0 to 10 | 0 to 2.0 |

|  | AF 5 | AF 6 | AF 7 | AF 8 |
|---|---|---|---|---|
| Alcohol a) [1] | 40 to 98 | 50 to 95 | 60 to 90 | 70 to 90 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Water | 0 to 30 | 0 to 20 | 0 to 10 | 0 to 2.0 |

|  | AF 9 | AF 10 | AF 11 | AF 12 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Water | 0 to 30 | 0 to 20 | 0 to 10 | 0 to 2.0 |

|  | AF 13 | AF 14 | AF 15 | AF 16 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) [5] | 1.0 to 25 | 5.0 to 20 | 7.0 to 18 | 8.5 to 15.5 |
| Water | 0 to 30 | 0 to 20 | 0 to 10 | 0 to 2.0 |

|  | AF 17 | AF 18 | AF 19 | AF 20 |
|---|---|---|---|---|
| Alcohol a) [1] | 40 to 98 | 50 to 95 | 60 to 90 | 70 to 90 |
| Anionic Polymer b) [2] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) | 0 to 2.5 | 0 to 1.5 | 0 to 0.5 | 0 to 0.1 |
| Water | 0 to 30 | 0 to 20 | 0 to 10 | 0 to 2.0 |

|  | AF 21 | AF 22 | AF 23 | AF 24 |
|---|---|---|---|---|
| Alcohol a) [1] | 40 to 98 | 50 to 95 | 60 to 90 | 70 to 90 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) | 0 to 2.5 | 0 to 1.5 | 0 to 0.5 | 0 to 0.1 |
| Water | 0 to 30 | 0 to 20 | 0 to 10 | 0 to 2.0 |

|  | AF 25 | AF 26 | AF 27 | AF 28 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) | 0 to 2.5 | 0 to 1.5 | 0 to 0.5 | 0 to 0.1 |
| Water | 0 to 30 | 0 to 20 | 0 to 10 | 0 to 2.0 |

|  | AF 29 | AF 30 | AF 31 | AF 32 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) [5] | 1.0 to 25 | 5.0 to 20 | 7.0 to 18 | 8.5 to 15.5 |
| Fatty substances d) | 0 to 2.5 | 0 to 1.5 | 0 to 0.5 | 0 to 0.1 |
| Water | 0 to 30 | 0 to 20 | 0 to 10 | 0 to 2.0 |

|  | AF 33 | AF 34 | AF 35 | AF 36 |
|---|---|---|---|---|
| Alcohol a) [1] | 15 to 95 | 25 to 90 | 25 to 90 | 25 to 85 |
| Anionic Polymer b) [2] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) [6] | 0 to 2.5 | 0 to 1.5 | 0 to 0.5 | 0 to 0.1 |
| Water | 0 to 30 | 0 to 20 | 0 to 10 | 0 to 2.0 |

|  | AF 37 | AF 38 | AF 39 | AF 40 |
|---|---|---|---|---|
| Alcohol a) [1] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) [6] | 0 to 2.5 | 0 to 1.5 | 0 to 0.5 | 0 to 0.1 |
| Water | 0 to 30 | 0 to 20 | 0 to 10 | 0 to 2.0 |

|  | AF 41 | AF 42 | AF 43 | AF 44 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) | 1.0 to 25 | 5.0 to 20 | 7.0 to 18 | 8.5 to 15.5 |
| Fatty substances d) [6] | 0 to 2.5 | 0 to 1.5 | 0 to 0.5 | 0 to 0.1 |
| Water | 0 to 30 | 0 to 20 | 0 to 10 | 0 to 2.0 |

|  | AF 45 | AF 46 | AF 47 | AF 48 |
|---|---|---|---|---|
| Alcohol a) [4] | 15 to 95 | 25 to 90 | 25 to 90 | 25 to 85 |
| Anionic Polymer b) [3] | 0.1 to 10 | 0.5 to 8.0 | 1.0 to 5.5 | 1.0 to 2.5 |
| Pigment c) [5] | 1.0 to 25 | 5.0 to 20 | 7.0 to 18 | 8.5 to 15.5 |
| Fatty substances d) [6] | 0 to 2.5 | 0 to 1.5 | 0 to 0.5 | 0 to 0.1 |
| Water | 0 to 30 | 0 to 20 | 0 to 10 | 0 to 2.0 |

[1] selected from aliphatic and/or aromatic alcohols having 2 to 8 carbon atoms,
[2] containing structural units of the formulas (I) to (III) with $R_1$, $R_2$ and $R_4$ each = H or $C_1$-$C_4$-alkyl group, $R^3$ = branched or unbranched, saturated or unsaturated $C_1$-$C_{12}$-alkyl group, $R_5$ = branched or unbranched, saturated or unsaturated $C_6$-$C_{14}$ alkyl group, A = O, S or NH,
[3] containing structural units of the formulas (I) to (III) with $R_1$, $R_4$ each = H, $R_2$ = methyl group, $R_3$ = *-$CH_2$—$C(CH_3)_2$ Group, $R_5$ = *-$C(CH_3)_2$—$CH_2$—$C(CH_3)_3$ Group, A = NH
[4] selected from ethanol,
[5] is selected from colored pigments based on mica or mica, which are coated with one or more metal oxides from the group including titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288) and/or iron blue (Ferric Ferrocyanide, CI 77510),
[6] selected from $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, hydrocarbons and mixtures thereof.

By using a special anionic polymer in conjunction with a particular alcohol, a uniform water-resistant pigment-containing film is formed. This film is extremely stable to external environmental influences, such as water, sweat and abrasion, but can be removed without residue from the keratinous surface by a single application of a surfactant-containing cleaning agent. In addition, the use of this polymer leads to a high hold and high flexibility of the polymer film formed. The application of this agent to the hair therefore leads in addition to a temporary color change at the same time a high and moisture-resistant hold. In addition, these agents have good cosmetic properties after their application to the skin and hair.

In addition to the components described above, the cosmetic compositions of the present disclosure may contain other ingredients. The group of these other ingredients includes, in particular, cosmetically effective auxiliaries and additives, such as surfactants, conditioners, thickeners and pH regulators.

The agents as contemplated herein may additionally contain a nonionic surfactant. Suitable nonionic surfactants are alkylpolyglycosides and alkylene oxide adducts of fatty alcohols and fatty acids with in each case 2 to 30 moles of ethylene oxide per mole of fatty alcohol or fatty acid. Preparations with good properties are also obtained if they contain as nonionic surfactants fatty acid esters of ethoxylated glycerol which have been reacted with at least 2 moles of ethylene oxide. The nonionic surfactants can be used in a total amount of from about 0.1 to about 45 wt.-%, for example from about 1 to about 30 wt.-%, such as from about 1 to about 15 wt. % based on the total weight of the agent.

The agents as contemplated herein may additionally contain a cationic surfactant. Cationic surfactants are understood to mean surfactants, i.e. surface-active compounds, each having one or more positive charges. Cationic surfactants contain only positive charges. Usually, these surfactants are composed of a hydrophobic part and a hydrophilic head group, whereby the hydrophobic part usually includes a hydrocarbon scaffolding (e.g. including one or two linear or branched alkyl chains), and the positive charge (s) are located in the hydrophilic head group.

Examples of cationic surfactants are
  quaternary ammonium compounds which as hydrophobic radicals may carry one or two alkyl chains having a chain length of 8 to 28 C atoms, quaternary phosphonium salts substituted with one or more alkyl chains having a chain length of 8 to 28 C atoms or tertiary sulfonium salts.

Furthermore, the cationic charge may also be in the form of an onium structure part of a heterocyclic ring (e.g., an imidazolium or a pyridinium ring). In addition to the functional unit which carries the cationic charge, the cationic surfactant may also contain other uncharged functional groups, as is the case, for example, with esterquats. The cationic surfactants can be used in a total amount of from about 0.1 to about 45 wt.-%, for example from about 1 to about 30 wt.-%, such as from about 1 to about 15 wt.-%, based on the total weight of the agent.

The use of anionic surfactants has been found to be negative in terms of the abrasion resistance of the pigments on the keratin fibers. For this reason, it is preferred not to use anionic surfactants in the agents of the present disclosure Anionic surfactants are surfactants with exclusively anionic charges (neutralized by a corresponding counter cation). Examples of anionic surfactants are fatty acids, alkyl sulfates, alkyl ether sulfates and ether carboxylic acids having 12 to 20 carbon atoms in the alkyl group and up to 16 glycol ether groups in the molecule.

In an exemplary embodiment, cosmetic agents in the present disclosure contain anionic surfactants in a total amount of from 0 to about 2.5% by weight.-%, for example from 0 to about 1.5 wt.-%, such as from 0 to about 0.5 wt.-%, for example from 0 to about 0.1 wt.-%, in particular of 0 wt. %, in each case based on the total weight of the cosmetic product.

The cosmetic agents as contemplated herein may furthermore comprise a zwitterionic and/or amphoteric surfactant. Suitable zwitterionic surfactants are betaines, N-alkyl-N, N-dimethylammonium glycinates, N-acyl-aminopropyl-N, N-dimethylammonium glycinates, and 2-alkyl-3-carboxymethyl-3-hydroxyethyl-imidazolines. A suitable zwitterionic surfactant is known by the INCI name Cocamidopropyl Betaine. Suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. Particularly suitable amphoteric surfactants are N-cocoalkylaminopropionate, cocoacylaminoethylaminopropionate and $C_{12}$-$C_{18}$-acylsarcosine.

The amphoteric and/or zwitterionic surfactants can be used in a total amount of from about 0.1 to about 45 wt.-%, for example from about 1 to about 30 wt.-%, such as from about 1 to about 15 wt.-% based on the total weight of the agent.

An advantage of the agents of the present disclosure is that they can be formulated in a variety of forms. When applied with a sponge or a small brush, very uniform color effects and water- and abrasion-fast dyeings can be achieved. Likewise it is also however possible to formulate the agents of the present disclosure as a spray. In particular, the dyeings obtained by the spray application are exemplified by a very high uniformity and water resistance.

Depending on the chosen application form, the agents of the present disclosure are adjusted to a specific viscosity. This is usually done by using one or more thickeners. Basically, the choice of thickeners is unlimited. It is possible to use either organic or purely inorganic thickeners.

Suitable thickeners are anionic, synthetic polymers; cationic synthetic polymers; naturally occurring thickeners such as nonionic guar gums, scleroglucan gums or xanthan gums, gum arabic, ghatti gum, karaya gum, gum tragacanth, carrageenan gum, agar agar, locust bean gum, pectins, alginates, starch fractions and derivatives such as amylose, amylopectin and dextrins, and cellulose derivatives such as methylcellulose, carboxyalkylcelluloses and hydroxyalkylcelluloses; nonionic, fully synthetic polymers, such as polyvinyl alcohol or polyvinylpyrrolidinone; and inorganic thickening agents, in particular phyllosilicates such as bentonite, especially smectites, such as montmorillonite or hectorite.

The viscosity of the agent by polysaccharides can be particularly easily and reproducibly set, in particular polysaccharides from the group of carboxy-$C_1$-$C_6$-alkyl celluloses, the hydroxy-$C_2$-$C_8$-alkylcelluloses, the alginic acids and/or xanthan gum.

By varying the amount of polysaccharide used, the agent can be formulated both as a gel for the brush or sponge application or else as a low-viscosity, sprayable solution. Neither the other recipe ingredients nor their amounts need to be adjusted, which is particularly advantageous in the production of the agents. In exemplary embodiment, an agent as contemplated herein additionally contains, as a thickener, a polysaccharide from the group of carboxy-$C_1$-$C_6$-alkyl celluloses, the hydroxy-$C_2$-$C_8$-alkylcelluloses containing alginic acid and/or xanthan gum.

In another exemplary embodiment, an agent of the present disclosure additionally contains, as a thickener, a polysaccharide from the group of hydroxy-$C_2$-$C_8$-alkylcelluloses.

The thickener or thickeners can be used in the present disclosure agents in a total amount of from about 0.1 to about 4.5 wt.-%, for example from about 0.15 to about 3.5 wt.-%, such as from about 0.2 to about 2.0 wt.-%, based on the total weight of the agent.

Some of the abovementioned thickeners—for example phyllosilicates, such as bentonite, especially smectite, such as montmorillonite or hectorite, can additionally serve as stabilizers in the present disclosure's agents.

In some cases, however, it has been observed that the usually cationically modified bentonites, garamites and/or Laponites can sometimes lead to stability losses of the agents of the present disclosure since they interact negatively with the anionic polymers of the cosmetic agents of the present disclosure.

This could be counteracted by the selection of special, organically modified hectorites. These are in an organic solvent as a gel and can be easily incorporated into the agents of the present disclosure. They additionally stabilize the agents of the present disclosure and prevent the sedimentation and/or the caking of the pigments during storage. Particularly suitable modified hectorites are, for example, those sold under the trade name Bentone® Gel IPM V (INCI name: isopropyl myristate, stearalkonium hectorite, propylene carbonate) available from Elementis.

To adjust the pH, the agents of the present disclosure may contain one or more alkalizing agents. The alkalizing agents which can be used as contemplated herein for setting the desired pH values can be selected from the group including ammonia, alkanolamines, basic amino acids and inorganic alkalizing agents such as alkali (earth) metal hydroxides, alkali (earth) metal metasilicates, alkaline (earth) metal phosphates and alkali (earth) metal hydrogen phosphates. To adjust the pH, the agents of the present disclosure may contain one or more acids. Suitable acids are, for example, organic acids such as alpha-hydroxycarboxylic acids or inorganic acids.

Furthermore, the agents may contain one or more nonionic polymers.

Suitable nonionic polymers are, for example:
Vinylpyrrolidone/vinyl ester copolymers,
Starch and its derivatives, especially starch ethers,
Shellac
Polyvinylpyrrolidones Further the present disclosure's agents may contain further active, auxiliary and additional agents, such as, for example linear cationic polymers like quarternised cellulosether, polysiloxane with quarternised groups, dimethyl-amino-ethylmethacrylat-Vinylpyrrolidinon-copolymers quarternised with diethylsulfate, vinylpyrrolidinon-Imidazolinium-methochloride-copolymers and quaternised polyvinylalcohol; zwitterionic and amphoteris polymers (which differ from the present disclosure's polymers); anionic polymers such as, for example, polyacryl acids or compound polyacryl acids; structurants such glucose, maleic acid and lactic acid, hair-conditioning compounds such as phospholipide, for example lecithin und cephalin; perfume oils, dimethylisosorbide and cyclodextrin; fibrous structure-enhancing ingredients, in particular mono-, di-und oligosaccharides such as, for example, glucose, galactose, fructose, fruite sugar and lactose; colorants for the agents; anti-dandruff ingredients such as piroctone olamine, zink omadine und climbazole; amino acids and oligopeptides; plant- or animal-based proteinhydrolysates, as well as in the form of their fatty acid condensation products or where appropriate anionically or cationically modified derivates; light stabilizers and UV-blockers; active ingredients such as Panthenol, pantothene acids, pantolactone, allantoine, pyrrolidinoncarbon acids and their salts as well as bisabolol; polyphenols, in particular hydroxycinnamic acid, 6,7-dihydroxycumarine, hydroxybenzoic acids, catechins, tannins, leucoanthocyanidins, anthocyanidins, flavanons, flavons and flavonols; ceramides or pseudoceramides; vitamins, provitamins and vitamin precursors; plant extracts; fats and waxes such as fatty alcohols, beeswax, montan wax und paraffins; swelling and penetration agents such as glycerine, propylenglycolmonoethylether, carbonates, hydrogencarbonates, guanidine, ureas such as primary, secondary and tertiary phosphates; opacifiers such as Latex, styrol/PVP-und styrol/acrylamide-copolymers such as PEG-3-distearate; propellants such as wie propane-butane mixtures, $N_2O$, dimethylether, $CO_2$ and air.

The choice of these other substances will be made by the experts according to the desired properties of the agents. With regard to further optional components and the amounts of these components used, reference is expressly made to the relevant manuals known to the experts. The additional active ingredients and auxiliaries can be used in the agents as contemplated herein in amounts of from about 0.0001 to about 25% by weight (wt.-%), for example from about 0.0005 to about 15 wt. %, based on the total weight of the cosmetic agent used.

When used in the form of a pump spray or in the form of an aerosol spray, the user can spray the agents of the present disclosure directly onto the dry hair or the skin and so produce the desired temporary color change.

In the case of application to the hair, the user can first—for example, by combing, back-combing, or by using a curling iron—style his hair and then spray on the agent. It is also possible first to spray the cosmetic agent of the present disclosure and then or in the meantime to bring the hairstyle by the aforementioned methods in the form. It is also possible first to spray on the agent and then or in the meantime to style the hair by the aforementioned methods.

In accordance with another exemplary embodiment, a method for the temporary alteration and coloring of keratinous fibers comprises the following steps:
a) providing a cosmetic agent as contemplated herein in the form of a gel, a pump spray or an aerosol spray,
b) applying, in particular spraying, the cosmetic agent provided in step a) to the keratinous fibers,
c) distributing the cosmetic agent applied in step b) on the keratinous fibers and styling of the keratinous fibers in the desired shape In principle, keratin-containing fibers are understood to mean all animal hairs, for example wool, horsehair, angora hair, furs, feathers and products or textiles made thereof. Preferably, however, the keratinous fibers are human hairs.

With regard to further embodiments of the method of the present disclosure, in particular with regard to the cosmetic agent used there, the same statements about the cosmetic agents contemplated herein apply mutatis mutandis.

In accordance with another exemplary embodiment a process for the temporary coloring of the skin comprises the following steps:
a) providing a cosmetic agent as contemplated herein in the form of a gel, a pump spray or an aerosol spray,
b) applying, in particular spraying, the cosmetic product provided in step a) to the skin,
c) distributing the applied in step b) cosmetic agent applied in step b) on the skin.

With regard to further embodiments of the process of the present disclosure, in particular with regard to the cosmetic agent used there, the same statements about the cosmetic agents contemplated herein apply mutatis mutandis.

A further exemplary embodiment relates to the use of an anionic polymer comprising a structural unit of the formula (I) and a structural unit of the formula (II) and a structural unit of the formula (III)

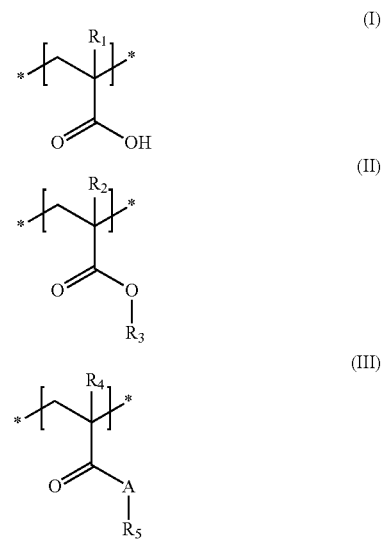

where
$R_1$, $R_2$ and $R_4$, independently of each other, represent a hydrogen atom or a $C_1$-$C_4$ alkyl group,
$R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group and A stands for an oxygen, sulfur or an NH group
in pigmented cosmetic agents to improve the water resistance of these agents. By improving the water resistance, it is understood in terms of the present disclosure that the use of these polymers leads to a reduction or the avoidance of the washing off of the pigments deposited on the surface when using water.

In an exemplary embodiment, anionic polymers are used which comprise a structural unit of the formula (I) and a structural unit of the formula (II) and a structural unit of the formula (III)

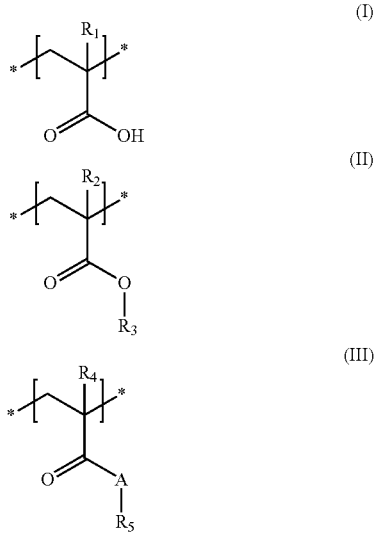

where
$R_1$ and $R_4$ each, independently of one another, represent hydrogen,
$R_2$ stands for a methyl group
$R_3$ is a *—$CH_2$—$CH(CH_3)_2$ group
$R_5$ represents a *—$C(CH_3)2$-$CH_2$—$C(CH_3)_3$ group, and
A stands for an NH group.

With regard to further embodiments of the applications contemplated herein, in particular with regard to the cosmetic agent used there, the same statements about the cosmetic agents as well as the statements made about the procedures apply mutatis mutandis.

The following examples illustrate the various embodiments, without limitation.

Examples

1. Water Resistance Test
To determine the water resistance of the dyeings, the following compositions were prepared (all figures in percent by weight, based on the total weight of the respective cosmetic agent):

| Raw material | V1 | E1 |
|---|---|---|
| Ethanol 99% denat | 80.7 | 80.7 |
| Anionic Polymer [1] | — | 1.5 |
| Pigment [2] | 11 | 11 |
| PVP/VA-Copolymer 60/40 W NP | 3.5 | 2.0 |
| Glycerin 99.5% | 2.0 | 2.0 |
| D-Panthenol 75% | 0.20 | 0.20 |
| Dehyquart A CA [3] | 0.45 | 0.45 |
| Stearamidopropyl Diemthylamine | 1.3 | 1.3 |
| KOH 50% | 0.20 | 0.20 |
| Perfume | 0.65 | 0.65 |

[2] Colorona Dark Blue, INCI name MICA, TITANIUM DIOXIDE, FERRIC FERROCYANIDE (Merck)
[3] INCI name: AQUA (WATER), CETRIMONIUM CHLORIDE (BASF).

Cosmetics V1 and E1 were obtained by mixing the above ingredients and applying the same to one strand of hair (Kerling 6-0, light brown) respectively. After drying, a uniform dark blue color with metallic luster was obtained in both cases. Subsequently, both strands were washed with water. While no influence on the coloration could be observed in the tress treated with the agent E1 as contemplated herein, the color achieved with the agent V1 was completely washed out. However, the dye obtained with the composition E1 could be removed without residue by a single wash with a surfactant-containing cleaning composition (shampoo). The use of the special anionic polymer therefore leads to an increased water resistance of the temporary hair dyeing in comparison to the nonionic PVP/VA polymer, but without adversely affecting the washability by employing surfactant-containing cleaning agents.

2. Further Example

| Raw material | E1 |
|---|---|
| Ethanol 96% denat | 85.45 |
| Anionic Polymer [1] | 0.75 |
| Pigment [4] | 7 |
| Glycerin 99.5% | 0.50 |
| D-Panthenol 75% | 0.20 |
| Perfume | 0.10 |
| Bentone Gel IPM V [5] | 6 |

[4] INCI name: MICA, CI 77491 (IRON OXIDES); Merck
[5] INCI name: ISOPROPYL MYRISTATE, STEARALKONIUM HECTORITE, PROPYLENE CARBONATE; Elementis While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic agent, comprising:
from about 40 to about 98 weight percent (wt. %) aliphatic alcohol having 2 to 8 carbon atoms, or from about 40 to about 98 wt. % aromatic alcohol having 2 to 8 carbon atoms, or from about 40 to about 98 wt. % of a combination thereof;
from about 0.1 to about 10 wt. % of an anionic polymer comprising a structural unit of the formula (I) and a structural unit of the formula (II) and a structural unit of the formula (III)

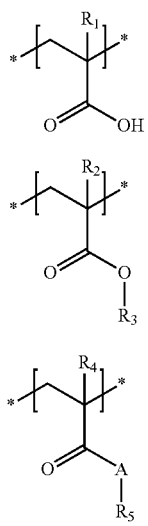

(I)
(II)
(III)

where $R_1$ is a hydrogen atom, $R_2$ is a methyl group, $R_3$ is a *—$CH_2$—$CH(CH_3)_2$ group, $R_4$ is a hydrogen atom, A stands for an NH group, and $R_5$ is a *—$C(CH_3)_2$—$CH_2$—$C(CH_3)_3$ group; and from about 1.0 to about 25 wt. % of a pigment, wherein the cosmetic agent comprises no more than about 2.0 wt. % water, and wherein each weight percent is based on the total weight of the cosmetic agent.

2. The cosmetic agent of claim 1, wherein the pigment is a mica or mica-based colored pigment comprising a metal oxide selected from the group consisting of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288), and iron blue (Ferric Ferrocyanide, CI 77510).

3. The cosmetic agent of claim 1, wherein the cosmetic agent comprises the aliphatic alcohol, and wherein the aliphatic alcohol is selected from the group consisting of ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, and glycerol.

4. The cosmetic agent of claim 1, wherein the cosmetic agent comprises the aromatic alcohol, and wherein the aromatic alcohol is selected from the group consisting of benzyl alcohol, phenoxyethanol, and phenylethyl alcohol.

5. The cosmetic agent of claim 1, wherein the cosmetic agent comprises the combination of aliphatic and aromatic alcohol, wherein the aromatic alcohol is selected from the group consisting of benzyl alcohol, phenoxyethanol, and phenylethyl alcohol, and wherein the aromatic alcohol is selected from the group consisting of benzyl alcohol, phenoxyethanol, and phenylethyl alcohol.

6. A method for water-resistant temporary coloring of hair, the method comprising the steps of:
providing a cosmetic agent in the form of a gel, a pump spray or an aerosol spray, the cosmetic agent comprising:
from about 40 to about 98 weight percent (wt. %) aliphatic alcohol having 2 to 8 carbon atoms, or from about 40 to about 98 wt. % aromatic alcohol having 2 to 8 carbon atoms, or from about 40 to about 98 wt. % of a combination thereof;

from about 0.1 to about 10 wt. % of an anionic polymer comprising a structural unit of the formula (I) and a structural unit of the formula (II) and a structural unit of the formula (III)

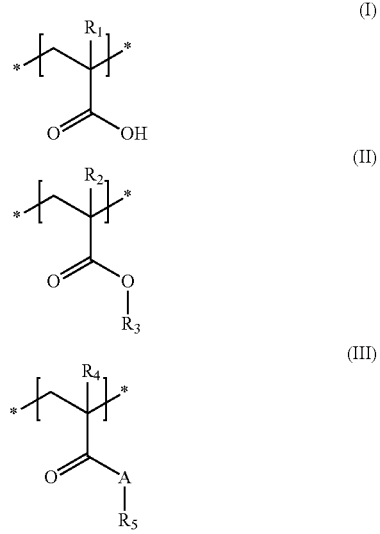

where $R_1$ is a hydrogen atom, $R_2$ is a methyl group, $R_3$ is a *—$CH_2$—$CH(CH_3)_2$ group, $R_4$ is a hydrogen atom, A stands for an NH group, and $R_5$ is a *—$C(CH_3)_2$—$CH_2$—$C(CH_3)_3$ group; and from about 1.0 to about 25 wt. % of a pigment, wherein the cosmetic agent comprises no more than about 2.0 wt. % water, and wherein each weight percent is based on the total weight of the cosmetic agent and applying the cosmetic agent to keratinous fibers of hair.

7. The method of claim 6, wherein the pigment is a mica or mica-based colored pigment comprising a metal oxide selected from the group consisting of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288), and iron blue (Ferric Ferrocyanide, CI 77510).

8. The method of claim 6, wherein the cosmetic agent comprises the aliphatic alcohol, and wherein the aliphatic alcohol is selected from the group consisting of ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, and glycerol.

9. The method of claim 6, wherein the cosmetic agent comprises the aromatic alcohol, and wherein the aromatic alcohol is selected from the group consisting of benzyl alcohol, phenoxyethanol, and phenylethyl alcohol.

10. The method of claim 6, wherein the cosmetic agent comprises the combination of aliphatic and aromatic alcohol, wherein the aromatic alcohol is selected from the group consisting of benzyl alcohol, phenoxyethanol, and phenylethyl alcohol, and wherein the aromatic alcohol is selected from the group consisting of benzyl alcohol, phenoxyethanol, and phenylethyl alcohol.

11. The method of claim 6, wherein applying comprises spraying.

* * * * *